(12) United States Patent
Timmins et al.

(10) Patent No.: US 6,660,300 B1
(45) Date of Patent: Dec. 9, 2003

(54) METHOD OF USE OF A BIPHASIC CONTROLLED RELEASE DELIVERY SYSTEM FOR HIGH SOLUBILITY PHARMACEUTICALS AND METHOD

(75) Inventors: Peter Timmins, Irby (GB); Andrew B. Dennis, Barnston (GB); Kiren A. Vyas, Canterbury (GB)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 10/224,945

(22) Filed: Aug. 21, 2002

Related U.S. Application Data

(60) Division of application No. 09/398,107, filed on Sep. 16, 1999, now Pat. No. 6,475,521, which is a continuation-in-part of application No. 09/044,446, filed on Mar. 19, 1998, now abandoned.

(51) Int. Cl.[7] .............................. A61K 9/22; A61K 9/26
(52) U.S. Cl. ........................ 424/469; 424/468; 424/470; 424/485; 424/486; 424/488; 514/772.3; 514/779; 514/781; 514/951
(58) Field of Search ................................ 424/469, 468, 424/457, 470, 484, 485, 486, 488

(56) References Cited

U.S. PATENT DOCUMENTS

| | | |
|---|---|---|
| 3,976,764 A | 8/1976 | Sumio et al. |
| 4,126,672 A | 11/1978 | Sheth et al. |
| 4,140,755 A | 2/1979 | Sheth et al. |
| 4,167,558 A | 9/1979 | Sheth et al. |
| 4,207,890 A | 6/1980 | Mamajek et al. |
| 4,351,825 A | 9/1982 | Sothmann et al. ............ 424/19 |
| 4,357,469 A | 11/1982 | Schor |
| 4,369,172 A | 1/1983 | Schor et al. |
| 4,434,153 A | 2/1984 | Urquart et al. |
| 4,704,285 A | 11/1987 | Alderman |
| 4,711,782 A | 12/1987 | Okada et al. |
| 4,767,627 A | 8/1988 | Caldwell et al. |
| 4,828,836 A | 5/1989 | Elger et al. |
| 4,844,905 A | 7/1989 | Ichikawa et al. |
| 4,954,298 A | 9/1990 | Yamamoto et al. |
| 5,007,790 A | 4/1991 | Shell |
| 5,169,638 A | 12/1992 | Dennis et al. |
| 5,232,704 A | 8/1993 | Franz et al. |
| 5,374,430 A | 12/1994 | Newton et al. |
| 5,484,608 A | 1/1996 | Rudnic et al. |
| 5,575,987 A | 11/1996 | Kamei et al. |
| 5,582,837 A | 12/1996 | Shell |
| 5,645,858 A | 7/1997 | Kotwal et al. |
| 5,824,344 A | 10/1998 | Palepu et al. |
| 5,955,106 A | 9/1999 | Moeckel et al. |
| 6,099,859 A | 8/2000 | Cheng et al. |
| 6,099,862 A | 8/2000 | Chen et al. |
| 6,340,475 B2 | 1/2002 | Shell et al. |
| 2001/0018070 A1 | 8/2001 | Shell et al. |

FOREIGN PATENT DOCUMENTS

| | | |
|---|---|---|
| DE | 4414544 C2 | 11/1994 |
| EP | 502642 A1 | 9/1992 |
| EP | 609961 A1 | 8/1994 |
| FR | 2594693 | 8/1987 |
| WO | 93/18755 | 9/1993 |
| WO | 94/27557 | 12/1994 |
| WO | 94/27589 | 12/1994 |
| WO | 96/08243 | 3/1996 |
| WO | 97/18814 | 5/1997 |
| WO | 98/55107 | 12/1998 |
| ZA | 95/7670 | 9/1995 |

OTHER PUBLICATIONS

Longer et al., Journal of Pharmaceutical Sciences, vol. 74, No. 4, pp. 406–411, Apr. 1985.
Davis et al., Pharmaceutical Research, vol. 3, No. 4, pp. 208–213, 1986.
Timmermans et al., Journal of Pharmaceutical Sciences, vol. 83, No. 1, pp. 18–24, Jan. 1994.
Chem. AG 126:229547, M. P. Goldson et al. 1997.
Chem. AG 132:83528, DePinko et al. 1999.
Noel, M. Journal of International Biomedical Information and Data, 1980 pp. 9–20.
Karttunen, P. et al. Int. J. Clin. Pharmacology, Therapy & Toxicology, vol. 21, No. 1, pp. 31–36 No date available.
Vidon, N. et al. Diabetes Research and Clinical Practice, 4 (1988) pp. 223–229.
Pentikainen, P.J. Int'l Journal of Clin. Pharm., Therapy and Toxicology, 24, No. 4, 1986, pp. 213–220.

*Primary Examiner*—James M. Spear
(74) *Attorney, Agent, or Firm*—Stephen B. Davis

(57) ABSTRACT

A biphasic controlled release delivery system for pharmaceuticals which have high water solubility, such as the antidiabetic metformin HCl salt, is provided which provides a dosage form that has prolonged gastric residence so that a dosing regimen of at least one gram metformin, once daily, may be achieved while providing effective control of plasma glucose. The delivery system includes (1) an inner solid particulate phase formed of substantially uniform granules containing a pharmaceutical having a high water solubility, and one or more hydrophilic polymers, one or more hydrophobic polymers and/or one or more hydrophobic materials such as one or more waxes, fatty alcohols and/or fatty acid esters, and (2) an outer solid continuous phase in which the above granules of inner solid particulate phase are embedded and dispersed throughout, the outer solid continuous phase including one or more hydrophobic polymers, one or more hydrophobic polymers and/or one or more hydrophobic materials such as one or more waxes, fatty alcohols and/or fatty acid esters, which may be compressed into tablets or filled into capsules. Methods for forming the so-described biphasic controlled release delivery system and using such biphasic controlled release delivery system for treating diabetes are also provided.

60 Claims, No Drawings

METHOD OF USE OF A BIPHASIC CONTROLLED RELEASE DELIVERY SYSTEM FOR HIGH SOLUBILITY PHARMACEUTICALS AND METHOD

REFERENCE TO OTHER APPLICATIONS

This is divisional of U.S. application Ser. No. 09/398,107 filed Sep. 16, 1999, U.S. Pat. No. 6,475,521 B1, which is a continuation-in-part of U.S. application Ser. No. 09/044,446 filed Mar. 19, 1998, now abandoned.

FIELD OF THE INVENTION

The present invention relates to a new dosage form for highly water soluble medicaments, such as the antidiabetic metformin, which provides for extended release of the drug and also for prolonged gastric residence, so that a dosing regimen of at least one gram metformin once daily, may be achieved while providing effective control of plasma glucose, and to a method for treating diabetes employing such dosage form.

BACKGROUND OF THE INVENTION

Metformin is an antihyperglycemic agent of the biguanide class used in the treatment of non-insulin dependent diabetes mellitus (NIDDM). It is usually marketed in the form of its hydrochloride salt as Glucophage® (TM-BMS).

Metformin hydrochloride has intrinsically poor permeability in the lower portion of the gastrointestinal tract leading to absorption almost exclusively in the upper part of the gastrointestinal tract. Its oral bioavailability is in the range of 40 to 60% decreasing with increasing dosage which suggests some kind of saturable absorption process, or permeability/transit time limited absorption. It also has a very high water solubility (>300 mg/ml at 25° C.). This can lead to difficulty in providing a slow release rate from a formulation and problems in controlling the initial burst of drug from such a formulation. These two difficulties are further compounded by the high unit dose, 500 mg per tablet, usually required for metformin hydrochloride (1997-PDR).

Drugs that have absorption limited to the upper gastrointestinal tract coupled with poor absorption in the distal small intestine, large intestine and colon are usually regarded as inappropriate candidates for formulation into oral controlled delivery systems. This limitation on absorption (for example, in the upper gastrointestinal tract) is referred to as the "absorption window".

The gastrointestinal tract functions to propel ingested material from the stomach (where digestion takes place) into the small intestine (where absorption principally occurs) and on to the large intestine (where water is absorbed/secreted as part of body fluid regulation processes). Residence time for non-digestible materials in the stomach depends on whether one is dealing with a fed or a fasted subject. Typical gastric emptying times for particulate material (greater than a few millimeters in diameter) varies from a few tens of minutes in the fasted state to a few hours in the fed state. Transit times through the small intestine are consistently of the order of 3 to 4 hours.

Oral controlled release delivery systems function by releasing their payload of drug over an extended period of time following administration. Thus, controlled release dosage forms may only spend a relatively short period in the regions of the gastrointestinal tract where good absorption of certain drugs can occur. The dosage form will pass on to regions of the intestine where absorption of certain drugs is poor or non-existent, still releasing its contained drug albeit with a significant percentage of its payload still to be delivered. Drug when released from the dosage form in the circumstances described will not be absorbed. Thus, administration of a drug subject to a window of absorption in a conventional controlled release delivery system can lead to subtherapeutic blood levels and ineffective treatment of the disease state for which the drug was intended.

Drugs with very high solubility in water (for example, greater than 100 mg/ml) can be difficult to formulate into a controlled release oral dosage form. Solubility is a driving force for a drug substance to dissolve in water; the greater the solubility the greater the rate of dissolution when all other factors are maintained constant.

In a controlled release dosage form, the formulator tries to reduce the rate of dissolution by, for example, embedding the drug in a polymeric matrix or surrounding it with a polymeric barrier membrane through which drug must diffuse to be released for absorption. To reduce the rate of release of drug from the dosage form to an appropriate level consistent with the blood level profile desired for a drug possessing very high water solubility, very large amounts of polymer would be required for the matrix or barrier membrane. If the total daily dose of drug to be delivered is of the order of only a few milligrams this may be feasible, but many drugs having the solubility properties described require total daily doses of the order of many hundreds of milligrams. Whilst it is possible to create oral controlled release dosage forms for such products by use of large amounts of polymer, an unacceptably large dosage form may result.

A further problem with highly water soluble drugs formulated into a controlled release dosage form is that a significant and variable "burst" of drug can occur from these systems. The burst of highly water soluble drug is the initial rapid release of drug that occurs from oral controlled release dosage forms when first contacting fluid, such as gastric fluids, prior to release controlling mechanisms of the dosage form establishing themselves and a stable release rate being provided. Hydration of any polymer matrix used to formulate the dosage form is a pre-requirement of establishing a stable release rate. Thus, a readily hydrating polymer is required to establish the desired stable release rate. However, if the polymer used is slow to hydrate, then an undesireable variable burst can occur.

Studies by Vidon et al (1) strongly suggest that there is permeability limited absorption of metformin. Perfusing drug into the jejunum via an intubation technique showed a 2.5 fold greater area under the plasma concentration-time profile (a measure of the quantity of drug absorbed) compared with similar introduction of drug into the ileum. Drug was not detectable in plasma when drug was perfused into the colon. Drug will transit down the small intestine following dissolution from an ingested dosage form and, if absorption rate is slow, it is possible that drug can reach regions of poor permeability before absorption of a given dose is complete. In such a case, increasing the given dose may be predicted to result in a reduction in the percentage of administered dose absorbed.

Improvements in the therapeutic regimes employing metformin might be achieved by a dosage form that allows a reduction in dosing frequency, providing patient convenience that would probably improve compliance. Conventional extended release formulations have been demonstrated to invariably compromise the availability of metformin (2), (2A), and (2B). This is probably because the dosage form carries a significant proportion of the drug content remaining to be released, as the dosage form is carried to regions of the gastrointestinal tract with very poor permeability to the drug. To reduce dosing frequency, the rate of release from the dosage form must be such as to extend effective plasma levels, but the potential for effective delivery at this rate is compromised by the combined influences of the significant reduction in permeability to the drug in passing from the proximal small intestine down to the colon and the limited residence time in the regions of the gastrointestinal tract where the drug is well absorbed. That transit time down the "useful" region of the gastrointestinal tract is only likely to be of the order of a few hours.

Maintained or even improved bioavailability from an extended release dosage form that releases metformin at a rate likely to provide the desired plasma levels of drug for an extended time period might, however, be possible from a dosage form that has extended residence time in the upper gastrointestinal tract, resisting mechanisms that promote normal transit time for solid materials. That this principle might work in practice was demonstrated in an in-house study where metformin was co-administered with propantheline, an agent that reduces gastrointestinal motility. Compared with giving metformin alone, the combination provided an increased AUC, a delayed tmax and an extended time period over which therapeutically beneficial plasma levels of drug were maintained.

Giving a drug such as metformin for the treatment of diabetes with a further drug, such as propantheline, not used for the treatment of diabetes and where the sole intent of using the second agent is to achieve extended residence time in the upper GI tract, has many disadvantages although it is likely to allow effective extended delivery of metformin to an optimal absorption site. The co-administered drug may have other undesirable pharmacological effects or side effects deleterious to the patients well being and detract from the improved quality of life offered by the treatment for their diabetes. Furthermore, it may be difficult or impossible to appropriately co-formulate the two agents due to chemical compatibility issues or solubility differences, the latter preventing the required release rate of agent influencing residence time in the upper GI tract. Thus, the patient could be required to take separate, multiple medications to achieve the desired effect. The timing of taking the two medications would be critical to effective delivery of the drug with the limited window of absorption and many patients may thus fail to take their medication correctly resulting in ineffective treatment of their diabetes.

Prior Art Gastro-Retentive Systems

It would be desirable to provide a dosage form that inherently has the property of extended gastric residence, possessing some resistance to the pattern of waves of motility present in the gastrointestinal tract that serve to propel material through it. There have been many attempts to provide for this, with varying degrees of success.

Possible approaches described in prior art include:
(1) Floating or buoyant systems:
    These are designed to have a low density and thus should float on gastric contents after administration until the system either disintegrates (and presumably the resultant particles empty from the stomach) or the device absorbs fluid to the point where its density is such that it loses buoyancy and can pass more easily from the stomach with a wave of motility responsible for gastric emptying.

(2) Bioadhesive systems:
    These are designed to imbibe fluid following administration such that the outer layer becomes a viscous, tacky material that adheres to the gastric mucosa/mucus layer. This should encourage gastric retention until the adhesive forces are weakened for example by continuing hydration of the outer layer of the device or by the persistent application of shear.

(3) Swelling and expanding systems:
    These are designed to be sufficiently small on administration so as not to make ingestion of the dosage form difficult (for example, less than approximately 23 mm long and less than 11 mm wide for an oval or capsule-shaped tablet). On ingestion they rapidly swell or unfold to a size that precludes passage through the pylorus until after drug release has progressed to a required degree. Gradual erosion of the system or its breakdown into smaller particles enables it to leave the stomach.

Re: (1) Buoyant/floating Systems

Buoyant systems designed to float on the gastric contents have been designed where buoyancy is created by low density of the formulation components. For example, Watanabe et al (3) used low density shells such as spherical polystyrene foam particles in which polymer and drug layers were loaded. Such a system has the required low density and will not need to disintegrate into small pieces to empty from the stomach, but may not have a controlled loss of density alternatively required for it to eventually exit from the stomach. It also has limited capacity for loading with drug in the thin layers that can be applied around the polystyrene shells. It would be difficult to also layer large amounts of polymer on such a system to retard the release of very water soluble drugs.

Sheth described hydrodynamically balanced systems including both capsules and tablets (4,5,6) which had low density to enable floating on the stomach contents and which slowly eroded after administration, losing buoyancy and being expelled from the stomach.

Buoyancy can also be combined with control of drug release at different pH values to make for a device with better control in case of drugs with very marked dependency of solubility on pH (7); hence dissolution of contained drug depending on environment pH.

These approaches may be applicable to many drugs dosed in doses of up to a maximum of a few hundred milligrams per day but may not be applicable to similar or higher dose levels of highly water soluble drugs. Where large amounts of polymer are needed to retard drug release as in the case of use of high water soluble drugs a capsule dosage form may not be possible on grounds of size. Furthermore, the relatively homogenous distribution of drug in the tablet versions of this technology would not readily control the burst effect seen with a very water soluble drug.

A bilayer tablet approach (8) where the buoyancy generation comes from a separate layer to the drug containing layer having a release rate controlling property might overcome some of the problems seen with the hydrodynamically balanced systems, but this type of system would probably only be able to carry low drug payloads due to size constraints.

Approaches involving in situ gas generation within the system, where the gas is trapped within the dosage form on generation, encouraging buoyancy, might offer improved control over degree, onset time and persistence of buoyancy. Ichikawa (9) described such a device with a drug loaded core surrounded by the gas generating layer, which in turn was surrounded by a polymeric layer responsible for controlling drug release from the system.

Such floating or buoyant dosage forms seem to have met with limited clinical success due to the requirement that such dosage forms be taken with a suitable amount of fluid (normal gastric contents could be as little as a few tens of milliliters so that the total amount of fluid thus available would not be conducive to performance of such systems even when taken with a draught of water). Davis et al (10) found no benefit of floating formulations over non-floating formulations when studied in vivo. Their performance may also be posture dependent. A patient sitting upright may ensure prolonged gastric residence of a buoyant dosage form, whereas a supine patient might allow ready presentation of the floating dosage form to the pylorus and thus allow rapid exit of the dosage form from the stomach (11). The physical size of such dosage forms seems to be as important if not more important as ability to float in encouraging prolonged gastric residence. Hence, floating/buoyant dosage forms might be expected to only have limited applications.

Re: (2) Bioadhesive Systems

Polycarbophil has been identified as a suitable polymer for encouraging adhesion of orally administered dosage forms to the gastric mucosa, thereby prolonging residence time for a system designed to slowly deliver drug to absorptive sites in the proximal small intestine (Longer et al, J. Pharm. Sci., 74, 406–411 (1985)). The success seen in animal models with such systems has been found not to translate to human subjects due to differences in mucous amounts, consistency and turnover between animals and humans. Bioadhesive systems allow dosage forms to adhere to mucous, not mucosa. The mucous layer in humans would appear to slough off readily, carrying any dosage form with it. Therefore, bioadhesive dosage forms would not appear to offer a solution for extended delivery of drug over a period of more than a few hours to the upper small intestine in humans.

Re: (3) Swelling/expanding Systems

Other solutions to encouraging prolonged gastric residence have included dosage forms that unfold rapidly within the stomach to a size that resists gastric emptying. Such systems retain their integrity for an extended period and will not empty from the stomach at all until breakdown into small pieces occurs. Caldwell (12) describes a cross shaped device made of erodible polymer and loaded with drug which is folded and inserted into a hard gelatin capsule. Following oral administration the gelatin shell disintegrates and the folded device opens out. With a minimum size of 1.6 cm and a maximum size of 5 cm it will not pass from the stomach through the pylorus until the polymer erodes to the point where the system is sufficiently small that it can be passed from the stomach. Such a system may in fact obstruct the pylorus or even open earlier or later than intended possibly causing obstruction in the esophagus or small intestine. As such, it may represent a potential hazard to the patient.

An alternate approach to using size to modulate gastric residence of a dosage form is to use a hydrophilic erodible polymer system that is of a convenient size for administration to humans. On imbibing fluid the system swells over a short period of time to a size that will encourage prolonged gastric retention, allowing sustained delivery of contained drug to absorption sites in the upper gastrointestinal tract. Because these systems are made of an erodible and hydrophilic polymer or polymer mixture, they readily erode over a reasonable time period to pass from the stomach. The time period of expansion is such that this will not occur in the esophagus and if the system passes into the intestine in a partially swollen state, the erodibility and elastic nature of the hydrated polymer will eliminate the chance of intestinal obstruction by the device.

Mamajek et al, U.S. Pat. No. 4,207,890, describes a system wherein a drug release rate controlling (metering) component and a swelling component are mixed with drug enclosed within a membrane. The swelling component draws in fluid through the membrane, which maintains system integrity during its functioning, and the drug metering component controls the rate of drug release through the membrane.

Urquart (13) describes a different approach which consists of a matrix of hydrogel that imbibes fluid to swell the system so that it reaches a size encouraging prolonged gastric retention. This matrix surrounds a plurality of tiny pills consisting of drug with a release rate controlling wall of fatty acid and wax surrounding each of the pills.

Shell (14,15,16) has described systems for delivering drugs for the treatment of diseases of the upper gastrointestinal tract or for delivering drugs that might be irritating or injurious to the gastrointestinal mucosa. A swelling hydrogel polymer has embedded within it drug particles that dissolve once the hydrogel matrix is hydrated. The swollen matrix is of a size to encourage gastric retention but only dissolved drug reaches the mucosa and this can be delivered in a sustained manner. Such a system thus does not insult the mucosa with solid particles of irritant drug and is suitable for delivering drug to upper gastrointestinal tract. These systems only apply in case of drugs of limited water solubility.

In the case of metformin, it is desirable to provide a dosage form that allows extended delivery of the drug and has a prolonged gastric residence via swelling of the system rather than unfolding or expanding of a folded device, and that may be manufactured on a commercial scale. The prolonged gastric residence time is required due to the window of absorption seen with metformin.

Another problem for extended delivery of metformin is its very high water solubility. High levels of polymer would be needed if many prior art approaches to provide the required release rate are employed. This could result in a rapid and variable initial release (burst) of drug from an extended release dosage form. The latter will thus give rise to difficulty in providing a true control of drug release and minimal inter-patient variability in drug plasma levels (arising from the possibility of variable burst of drug from tablets given to different patients).

Prior Art Controlled Release Systems for Very Soluble Drugs

Typical prior art techniques for creating a controlled release oral dosage form would involve either matrix systems or multi particulate systems. Matrix systems may be formulated by homogeneously mixing drug with hydrophilic polymers, such as hydroxypropylmethylcellulose, hydroxypropylcellulose, polyethylene oxide, carbomer, certain methacrylic acid derived polymers, sodium alginate, or mixtures of components selected from these, and compressing the resultant mixture into tablets (employing some other excipients where needed). Hydrophobic polymers, such as ethyl cellulose, certain polymeric methacryllc acid esters, cellulose acetate butyrate, poly(ethylene-co-vinyl-acetate) may be uniformly incorporated with the above materials to give additional control of release. A further alternative involves embedding drug within a wax based tablet, by granulation or simply mixing of drug with a wax, such as carnauba wax, microcrystalline wax or commercially available purified fatty acid esters. As noted above, it may not be possible to use these approaches with very highly water soluble drugs.

Multi particulate systems consist of a dosage form based on a plurality of drug loaded spheres, prepared by layering drug onto a core, usually a sugar-starch mixture sphere of around 0.8 mm diameter, until a sufficient level is reached, and then providing a drug release barrier around the drug-loaded sphere. Drug-loaded spheres can also be made by wet massing a mixture of drug and excipients, forcing the wet mass through a perforated screen to form short strands which are rounded in a spheronisation apparatus before drying and having the drug release barrier applied. The drug release barrier can be a wax, such as carnauba wax or glyceryl fatty acid esters, or a polymeric barrier, such as a mixture of ethyl cellulose and hydroxypropylmethylcellulose. These work well for moderately soluble drugs with doses in the units of milligrams to less than a few hundred milligrams per day.

In several examples, prior art systems seem to provide a controlled release formulation of a very water soluble drug by improving the multi particulate system approach. Fisher discloses a multi particulate system for highly soluble drugs especially opiate agonists (17) based on drug containing cores surrounded by a drug release controlling barrier which has the property of being partially soluble at a highly acidic pH.

Hansraj (18) coats drug loaded cores with methacrylic or acrylic acid derived polymers whose properties are modified by inclusion of at least one anionic surfactant. In such a system, drug release of highly water soluble drugs is controlled without having to resort to the use of thick coatings on the release rate controlling layer.

Rollet (19) achieves prolonged release of a drug from a multi particulate formulation based on fine particles of hydrophilic and hydrophobic silicas or silicates. Presumably, this system would function for drugs of high water solubility.

Multi particulate systems are usually filled into capsules to provide unit dose forms because of the damage caused to such particles in trying to compress them into tablets. Total dose contained in a single unit is constrained by the loading possible in a hard gelatin capsule of easily swallowable size and is usually not more than a few hundred milligrams.

Single unit controlled release systems applicable to highly water soluble drugs include the application of multiple layers around a dose form as described by Howard (20). Where coating is not employed, special mixtures of polymers or formation of a complex with the drug have been used. Macrae (21) uses mixtures of polyethylene oxide and hydroxypropylmethylcellulose with optional enteric polymers to produce a constant release rate for highly water soluble drugs. Belenduik (22) combines the highly water soluble drug with a hydrophilic polymer based on acrylic acid and disperses this in a hydrophobic matrix.

Variations of Alza osmotic systems have been described suitable for highly water soluble drugs such as venlafaxine hydrochloride (23). These systems need two layers, a drug layer and an osmotically driven displacement layer all surrounded by a water permeable/drug impermeable membrane with an exit passage in this membrane for the drug.

Granules of highly water soluble clavulanate were prepared (24) having to employ a barrier layer of a hydrophobic waxy material in order to provide for controlled release of this material when co-formulated with controlled release amoxycillin trihydrate granules in capsule or compressed tablet.

DESCRIPTION OF THE INVENTION

In accordance with the present invention, a novel way has been found of formulating drug with high water solubility and a limited window of absorption such as metformin or a salt thereof which has a window of absorption in the upper gastrointestinal tract, to provide a dosage form that inherently has prolonged gastric residence. This is accomplished (a) without need for co-administration of a drug such as propantheline, and (b) without need for low density formulation or gas generation within the formulation, The formulation of the invention (a) achieves extended gastric residence by virtue of size but will degrade in vivo so as not to have potential for causing gastric or intestinal obstruction, and (b) controls drug release adequately where the initial burst of drug is under control. The formulations of the invention will provide for an extended release formulation of drug with minimal interpatient variability in pharmacokinetic parameters.

In the case of metformin, the formulation of the invention allows a patient a dosing regimen of at least one gram metformin, once-daily, preferably from about 1 to about 3 grams, once daily, in the form of one or more tablets and/or one or more capsules, while providing effective control of plasma glucose. The metformin formulations of the invention may be administered once daily at the above dosages to effectively treat diabetes while avoiding problems which may be associated with high plasma metformin levels as may be encountered with conventional metformin formulations, while providing optimum therapeutic control.

The invention is applicable to all drugs having high water solubility and a limited window of absorption.

The biphasic controlled release delivery system of the invention is a heterogeneous two phase system which includes (1) an inner solid particulate phase in the form of individual granules or particles containing (a) drug which has a high water solubility, preferably, metformin or a salt thereof, and a limited window of absorption (such as in the upper gastrointestinal tract), and (b) an extended release material formed of one or more hydrophilic polymers, and/or one or more hydrophobic polymers, and/or one or more other type hydrophobic materials (such as one or more waxes, fatty alcohols and/or fatty acid esters), and (2) an outer solid continuous phase in which granules or particles of inner solid particulate phase are dispersed and embedded, the outer solid continuous phase which primarily is formed of an extended release material formed of one or more hydrophilic polymers, and/or one or more hydrophobic polymers, and/or one or more other type hydrophobic materials (such as one or more waxes, fatty alcohols and/or fatty acid esters).

The biphasic controlled release formulation of the invention is particularly adapted for delivery of high water soluble drugs, such as metformin and pharmaceutically acceptable salts thereof, in controlled and extended manner without significant initial burst of drug, and wherein release of drug (liberated from the individual dispersed particles forming the inner solid particulate phase) is effectively controlled. Drug upon being released from the particles of the inner phase, in effect, migrates through the outer solid continuous phase and then is released from the formulation into the upper gastrointestinal tract to be available for absorption.

As indicated, the inner solid particulate phase will be formed of individual discrete particles or granules each of which contains drug and one or more polymeric materials and/or other hydrophobic-type materials. In effect, the components of the inner solid particulate phase are in particulate association without having a barrier layer around the individual particles or granules.

The outer solid continuous phase is preferably a continuous phase or matrix having the particles or granules including drug (forming the inner solid phase) dispersed throughout and embedded in the continuous outer solid phase.

In addition, in accordance with the present invention, a method for lowering insulin resistance or treating diabetes is provided wherein the biphasic controlled release formulation of the invention containing an antidiabetic pharmaceutical is administered to a patient in need of treatment.

The term "diabetes" as employed herein refers to type 2 diabetes and type 1 diabetes, usually type 2 diabetes.

The antidiabetic pharmaceutical employed is preferably a biguanide, preferably metformin or a pharmaceutically acceptable salt thereof such as the hydrochloride, hydrobromide, fumarate, succinate, p-chlorophenoxy acetate or embonate, all of which are collectively referred to as metformin. The fumarate and succinate salts are preferably the metformin (2:1) fumarate, and the metformin (2:1) succinate disclosed in U.S. application Ser. No. 09/262,526 filed Mar. 4, 1999. Metformin hydrochloride salt is preferred.

In another aspect of the present invention, a method is provided for lowering insulin resistance or treating diabetes wherein the biphasic controlled release formulation of the invention contains metformin and is administered in a dosing regimen of at least one gram metformin, once daily, preferably from about 1 to about 3 grams, once daily, to a patient in need of treatment.

The term "extended release material" as present in the inner solid particulate phase and the outer solid continuous phase refers to one or more hydrophilic polymers and/or one or more hydrophobic polymers and/or one or more other type hydrophobic materials, such as, for example, one or more waxes, fatty alcohols and/or fatty acid esters. The "extended release material" present in the inner solid particulate phase may be the same as or different from the "extended release material" present in the outer solid continuous phase. However, it is preferred that the "extended release material" present in the inner solid particulate phase be different from the "extended release material" present in the outer solid continuous phase.

The term "high water solubility" or similar term when characterizing a drug, medicament or pharmaceutical for use in the formulation of the invention refers to a solubility in water at ambient temperature of at least about 50 mg/ml $H_2O$, preferably at least about 100 mg/ml $H_2O$ or more, and more preferably greater than 150 mg/ml.

The term "limited window of absorption" or similar term when characterizing a drug, medicament or pharmaceutical for use in the formulation of the invention refers to an oral bioavailability of less than about 75%, usually less than about 60%, usually decreasing with increasing dose, and almost invariably having permeability/transit time limited absorption.

The biphasic controlled release system of the invention will include the inner solid particulate phase in a weight ratio to the outer solid continuous phase within the range from about 0.5:1 to about 4:1, preferably from about 0.8:1 to about 2:1.

The inner solid particulate phase will contain drug in an amount within the range from about 10 to about 98% by weight, preferably from about 15 to about 95% by weight, and extended release material in the form of hydrophilic polymers and/or hydrophobic polymers and/or other hydrophobic material in an amount within the range from about 5 to about 95% by weight, preferably from about 7 to about 85% by weight, the above % being based on the weight of the inner solid particulate phase. Where mixtures are employed, the hydrophilic polymer will be employed in a weight ratio to hydrophobic polymer and/or other hydrophobic material within the range from about 0.05:1 to about 19:1, preferably from about 0.1:1 to about 10:1.

The particles or granules of the inner solid particulate phase will have a mean particle size within the range from about 30 μm to about 0.8 mm, and preferably from about 50 μm to about 0.5 mm.

The outer solid continuous phase will contain extended release material (preferably different from that employed in the inner solid particulate phase) in the form of one or more hydrophilic polymers and/or hydrophobic polymers and/or other hydrophobic material in an amount within the range from about 40 to about 100%, preferably from about 60 to about 100% (based on the weight of the outer solid continuous phase).

The outer solid continuous phase may contain mixtures of two or more extended release materials in the form of one or more hydrophilic polymer and/or hydrophobic polymer and/or other hydrophobic material in a weight ratio of hydrophilic polymer to hydrophobic polymer or other hydrophobic material within the range from about 200:1 to about 0.05:1, preferably from about 100:1 to about 0.1:1.

The pharmaceutical formulation of the invention will have a total polymer extended release material content (including hydrophilic polymers and/or hydrophobic polymers and/or other hydrophobic material present in the inner solid particulate phase and hydrophilic polymer and/or hydrophobic polymers and/or other hydrophobic material present in the outer solid continuous phase) within the range from about 25 to about 75% by weight, preferably from about 30 to about 65%, more preferably from about 35 to about 60% by weight based on the total weight of the pharmaceutical formulation.

Hydrophilic polymers which may be employed in the inner solid particulate phase and/or outer solid continuous phase include, but are not limited to hydroxypropylmethylcellulose, hydroxypropylcellulose, sodium carboxymethylcellulose, carboxymethylcellulose calcium, ammonium alginate, sodium alginate, potassium alginate, calcium alginate, propylene glycol alginate, alginic acid, polyvinyl alcohol, povidone, carbomer, potassium pectate, potassium pectinate, and the like.

Hydrophobic polymers which may be employed in the inner solid particulate phase and/or outer solid continuous phase include, but are not limited to ethyl cellulose, hydroxyethylcellulose, ammonio methyacrylate copolymer (Eudragit RL™ or Eudragit RS™), methyacrylic acid copolymers (Eudragit L™ or Eudragit S™), methacrylic acid-acrylic acid ethyl ester copolymer (Eudragit L 100-5™), methacrylic acid esters neutral copolymer (Eudragit NE 30D™), dimethylaminoethylmethacrylate-methacrylic acid esters copolymer (Eudragit E 100™), vinyl methyl ether/maleic anhydride copolymers, their salts and esters (Gantrez™).

Other hydrophobic materials which may be employed in the inner solid particulate phase and/or outer solid continuous phase include, but are not limited to waxes such as beeswax, carnauba wax, microcrystalline wax, and ozokerite; fatty alcohols such as cetostearyl alcohol, stearyl alcohol; cetyl alcohol and myristyl alcohol; and fatty acid esters such as glyceryl monostearate, glycerol monooleate, acetylated monoglycerides, tristearin, tripalmitin, cetyl esters wax, glyceryl palmitostearate, glyceryl behenate, and hydrogenated castor oil.

Where hydrophilic polymers and/or hydrophobic polymers are used in the inner solid particulate phase and/or the outer solid continuous phase, such polymers can be ionic or non-ionic, preferably ionic for the inner solid particulate phase and preferably non-ionic for the outer solid continuous phase.

Preferred ionic polymers for use in the inner solid particulate phase include sodium alginate, carbomer (Carbopol™), calcium carboxymethylcellulose, or sodium carboxymethylcellulose, xanthan gum, methacrylic acid-acrylic acid ethyl ester copolymer, dimethylaminoethylmethacrylate-methacrylic acid esters copolymer, cellulose acetate phthalate, hydroxypropylmethylcellulose phthalate, hydroxypropylmethylcellulose trimellitate, and hydroxypropylmethylcellulose maleate, with sodium carboxymethylcellulose being particularly preferred.

Preferred non-ionic polymers for use in the outer solid continuous phase are those which assure rapid hydration of the outer solid continuous phase to minimize a variable and significant burst of drug, yet effectively control the release of drug being liberated from the discrete particles or granules forming the inner solid particulate phase. The liberated drug will migrate through the non-ionic polymers forming the outer solid continuous phase before being released from the dosage form and being available for absorption. Preferred polymers for the outer solid phase with the appropriate hydration characteristics include hydroxypropylmethyl cellulose 2208 USP (hydroxypropylmethylcellulose with a methoxyl content of 19–24% and a hydroxypropyl content of 4–12%), viscosity grades ranging from about 4000 to about 100,000 cps and hydroxypropylmethylcellulose 2910 USP (hydroxypropyl-methylcellulose with a methoxy content of 28–30% and a hydroxypropyl content of 7–12%), viscosity grades ranging from about 3 to about 150 cps. In particular preferred embodiments of the outer solid phase, the above preferred polymers are used in admixture in weight ratios of hydroxypropylmethylcellulose 2208 USP:hydroxypropylmethylcellulose 2910 USP within the range from about 25:1 to about 50:1, preferably from about 30:1 to about 40:1.

Preferred biphasic controlled extended release delivery systems in accordance with the present invention are as follows.

| A. | Inner Solid Particulate Phase | % by Weight of Inner Solid Particulate Phase |
|---|---|---|
| | (1) Metformin HCl (or other salt such as succinate or fumarate) | 55 to 98 |
| | (2) Polymer or Hydrophobic Material | 5 to 95 |
| | Preferred: ethylcellulose and/or sodium carboxymethylcellulose and/or glyceryl monostearate (Average Particle Size of granules forming inner solid particulate phase: 0.05 to 2.0 mm) | 5 to 45 |

| B. | Outer Solid Continuous Phase | % by Weight of Outer Solid Continuous Phase |
|---|---|---|
| | Polymer and/or Hydrophobic Material: Preferred | 40 to 100 |
| | (1) Hydroxypropylmethyl-cellulose 2208USP (100,000 cps) | 60 to 100 |
| | (2) Hydroxypropylmethyl cellulose 2910 USP (5 cps) | 1 to 30 |
| | Weight Ratio of Inner Solid Phase: Outer Solid Phase | 0.5:1 to 1.5:1 |

| C. | Optional Ingredients | % by Weight of Outer Solid Continuous Phase |
|---|---|---|
| | Lubricant (e.g. Mg Stearate) | 0.02 to 1 |
| | Compression aid (e.g. Microcrystalline cellulose) | 0 to 30 |

The preferred drug (having high water solubility) or use herein is metformin or pharmaceutically acceptable salts thereof, including the hydrochloride salt and dibasic salts such as metformin (2:1) fumarate and metformin (2:1) succinate as described in pending U.S. application Ser. No. 09/262,526 filed Mar. 4, 1999, now U.S. Pat. No. 6,031,044, which is incorporated herein by reference.

Most preferred are the metformin hydrochloride salt, metformin (2:1) succinate salt, and metformin (2:1) fumarate salt.

Where desired, metformin or a salt thereof may be used in combination with another antihyperglycemic agent and/or a hypolipidemic agent which may be administered orally in the same dosage form in accordance with the invention, a separate oral dosage form or by injection. The metformin or salt thereof will be employed in a weight ratio to the other antihyperglycemic agent and/or hypolipidemic agent within the range from about 0.01:1 to about 300:1, preferably from about 0.05:1 to about 250:1.

It is believed that the use of the metformin or salt thereof in combination with another antihyperglycemic agent produces antihyperglycemic results greater than that possible from each of these medicaments alone and greater than the combined additive antihyperglycemic effects produced by these medicaments.

In addition, in accordance with the present invention a method is provided for lowering insulin resistance or treating hyperglycemia including type 2 diabetes (NIDDM) and/or type 1 diabetes (IDDM) wherein a therapeutically effective amount of the biphasic formulation of the invention containing metformin or a salt thereof, optionally in combination with another antihyperglycemic agent and/or a hypolipidemic agent, is administered to a patient in need of treatment.

The other antihyperglycemic agent may be an oral antihyperglycemic agent preferably a sulfonyl urea such as glyburide (also known as glibenclamide), glimepiride (disclosed in U.S. Patent No. 4,379,785), glipizide, gliclazide or chlorpropamide, other known sulfonylureas or other antihyperglycemic agents which act on the ATP-dependent channel of the β-cells, with glyburide being preferred.

The metformin or salt thereof will be employed in a weight ratio to the sulfonyl urea in the range from about 300:1 to about 50:1, preferably from about 250:1 to about 75:1.

The oral antihyperglycemic agent may also be a glucosidase inhibitor such as acarbose (disclosed in U.S. Pat. No. 4,904,769) or miglitol (disclosed in U.S. Pat. No. 4,639,436), which may be administered in a separate oral dosage form.

The metformin salt thereof will be employed in a weight ratio to the glucosidase inhibitor within the range from about 300:1 to about 2:1, preferably from about 200:1 to about 25:1.

The metformin or salt thereof may be employed in combination with a thiazolidinedione oral anti-diabetic agent (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016) Glaxo-Welcome's GL-262570, englitazone (CP-68722, Pfizer) or darglitazone (CP-86325, Pfizer).

The metformin or salt thereof will be employed in a weight ratio to the thiazolidinedione in an amount within the range from about 75:1 to about 0.1:1, preferably from about 5:1 to about 0.5:1.

The sulfonyl urea and thiazolidinedione in amounts of less than about 150 mg oral anti-diabetic agent may be incorporated in a single tablet with the biphasic controlled release formulation of the invention as a separate rapidly dissolving layer.

The metformin or salt thereof may also be employed in combination with a non-oral antihyperglycemic agent such as insulin or with glucagon-like peptide-1 (GLP-1) such as GLP-1(1–36) amide, GLP-1(7–36) amide, GLP-1(7–37) (as disclosed in U.S. Pat. No. 5,614,492 to Habener, the disclosure of which is incorporated herein by reference), which may be administered via injection, or by transdermal or buccal devices.

Where present, the sulfonyl ureas, such a s glyburide, glimepiride, glipyride, glipizide, glipizide, chlorpropamide and gliclazide and the glucosidase inhibitors acarbose or miglitol may be employed in formulations as described above and in amounts and dosing as indicated in the Physician's Desk Reference.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. No. 5,346,701 (TheraTech), U.S. Pat. Nos. 5,614,492 and 5,631,224 which are incorporated herein by reference.

The hypolipidemic agent which may be optionally employed in combination with metformin or a salt thereof may include MTP inhibitors, HMG CoA reductase inhibitors, squalene synthetase inhibitors, fibric acid derivatives, ACAT inhibitors, cholesterol absorption inhibitors, ileal Na+/bile acid cotransporter inhibitors, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,563,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is
9-[4-[4-[[2-(2,2,2-Trifluoroethoxy)benzoyl]amino]-1-piperidinyl]butyl]-N-(2,2,2-trifluoroethyl)-9H-fluorene-9-carboxamide

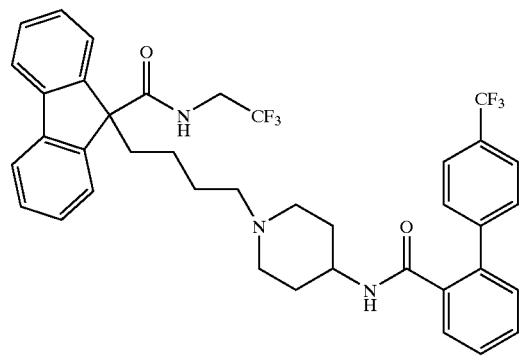

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, as well as other known HMG CoA reductase inhibitors.

In addition, phosphinic acid compounds useful in inhibiting HMG CoA reductase suitable for use herein are disclosed in GB 2205837.

The squalene synthetase inhibitors suitable for use herein include, but are not limited to, α-phosphonosulfonates disclosed in U.S. Pat. No. 5,712,396, those disclosed by Biller et al, J. Med. Chem., 1988, Vol. 31, No. 10, pp 1869–1871, including isoprenoid (phosphinylmethyl)phosphonates as well as other squalene synthetase inhibitors as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58–035, American Cyanamid CL-277,082 and CL-283,546 (disubstituted urea derivatives), nicotinic acid, acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62.

The cholesterol absorption inhibitor may be Schering-Plough's SCH 48461 or as disclosed in Atherosclerosis 115, 45–63 (1995) or J. Med. Chem. 41, 973 (1998).

The ileal Na$^+$/bile acid cotransporter inhibitor may be as disclosed in Drugs of the Future, 24, 425–430 (1999).

Preferred hypolipidemic agents are pravastatin, lovastatin, simvastatin, atorvastatin, fluvastatin and cerivastatin.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolypidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic gent will be as disclosed in the various patents, papers and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 100 mg/kg and preferably from about 0.1 mg/kg to about 75 mg/kg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For parenteral administration, the MTP inhibitor will be employed in an amount within the range of from about 0.005 mg/kg to about 10 mg/kg and preferably from about 0.005 mg/kg to about 8 mg/kg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The metformin or salt thereof and the hypolipidemic agent may be employed together in the same oral dosage form or in separate oral dosage forms taken at the same time.

The compositions described above may be administered in the dosage forms as described above in single or divided doses, once daily and up to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin.

The following additional type high water soluble drugs may be employed in the biphasic controlled release delivery system of the invention:

pravastatin;

antihypertensives and antidepressants related to guanethidine (as disclosed in U.S. Pat. No. 2,928,829) and related to guanoxyfen (as disclosed in BE612362);

antibiotics and viricides such as related to amidinomycin (as disclosed in JP 21,418);

stallimycin (as disclosed in DE 1,039,198);

Arphamenine B (as disclosed in published European Patent Application 85/133550A2);

chitinovorin-A (as disclosed in published European Patent Application 85/150,378A2 and U.S. Pat. No. , 4,723, 004);

streptomycin (as disclosed in U.S. Pat. No. 2,868,779);

SB-59 (as disclosed in Justus Liebigs, Ann. Chem. (1973) 7, 1112–1140);

TAN-1057-A (as disclosed in U.S. Pat. No. 4,971,965);

streptoniazid (as disclosed in J. Am. Chem. Soc. (1953) 75, 2261);

immunostimulants related to ST-789 (as disclosed in published European Patent Application 88/260588);

peptide hydrolase inhibitors related to nafamastat (as disclosed in U.S. Pat. No. 4,454,338);

gabexate (as disclosed in U.S. Pat. No. 3,751,447);

sepimostat (as disclosed in U.S. Pat. Nos. 4,777,182 and 4,820,730);

Factor Xa inhibitors related to DX-9065a (as disclosed in published European Patent Application 92/0540051);

anti-inflammatory agents related to paranyline as disclosed in U.S. Pat. No. 2,877,269;

peptidyl aldehydes (as disclosed in WO94/13693);

antianaphylactics related to GMCHA-TBP (Batebulast) (as disclosed in U.S. Pat. No. 4,465,851);

anti-ulcer agents related to benexate (as disclosed in U.S. Pat. No. 4,348,410);

deoxyspergualin (as disclosed in U.S. Pat. Nos. 4,518, 532, 4,658,058 and 4,983,328); and arginine.

Other water-soluble drugs suitable for use herein include peptides preferably have a molecular weight from about 100 to 10,000, more preferably from about 100 to about 6,000 and having from 2 to 35 amino acid moieties. Higher molecular weight peptides, even those with a molecular weight of above 10,000, up to about 50,000, may also be accommodated in biphasic formulations of the present invention.

Suitable small peptides have from about 2 to about 10, more preferably from about 2 to about 6 amino acid moieties. Preferred small peptides include the fibrinogen receptor antagonists (RGD containing peptides) which are tetrapeptides with an average molecular weight of about 600. These peptide antagonists are highly potent platelet aggregation inhibitors at plasma levels as low as 1 pmol/mL. Preferred fibrinogen antagonists include the peptide cyclo (S,S)-$N^a$-acetyl-Cys-($N^a$-methyl)Arg-Gly-Asp-Pen-$NH_2$ (Ali et al, EP 0341915, whose disclosure is herein incorporated by reference) and the peptide cyclo(S,S)-(2-mercapto) benzoyl-($N^a$-methyl)Arg-Gly-Asp-(2-mercapto)-phenylamide (EP 0423212:, whose disclosure is herein incorporated by reference). Other fibrinogen antagonists useful in the present invention are those peptides disclosed by Pierschbacher et al, WO 89/05150 (US/88/04403); Marguerie, EP 0275748; Adams et al, U.S. Pat. No. 4,857, 508; Zimmerman et al, U.S. Pat. No. 4,683,291; Nutt et al, EP 0410537, EP 0410539, EP 0410540, EP 0410541, EP 0410767, EP 0410833, EP 0422937 and EP 0422938; Ali et al, EP 0372486; Ohba et al, WO 90/02751 (PCT/JP89/ 00926); Klein et al, U.S. Pat. No. 4,952,562; Scarborough et al, WO 90/15620 (PCT/US90/03417); Ali et al, PCT/US90/ 06514 and PCT/US92/00999; the peptide-like compounds disclosed by Ali et al, EP 0381033 and EP 0384362; and the RGD peptide cyclo-$N^a$-acetyl-Cys-Asn-Dtc-Amf-Gly-Asp-Cys-OH (in which Dtc is 4,4'-dimethylthia-zolidine-5-carboxylic acid and Amf is 4-aminomethylphenyl-alanine).

The RGD peptide may be usefully included in the formulation of the invention in an amount up to about 600 mg/g of the hydrophilic phase or from 0.1 to 60 mg/g of the formulation.

Other peptides useful in the present invention include, but are not limited to, other RGD containing peptides such as those disclosed by Momany, U.S. Pat. No. 4,411,890 and U.S. Pat. No. 4,410,513; Bowers et al, U.S. Pat. No. 4,880, 778, U.S. Pat. No. 4,880,777, U.S. Pat. No. 4,839,344; and WO 89/10933 (PCT/US89/01829); the peptide Ala-His-D-Nal-Ala-Trp-D-Phe-Lys-$NH_2$ (in which Na1 represents b-naphthyl-alanine) and the peptides disclosed by Momany, U.S. Pat. No. 4,228,158, U.S. Pat. No. 4,228,157, U.S. Pat. No. 4,228,156, U.S. Pat. No. 4,228,155, U.S. Pat. No. 4,226,857, U.S. Pat. No. 4,224,316, U.S. Pat. No. 4,223,021, U.S. Pat. No. 4,223,020, U.S. Pat. No. 4,223,019 and U.S. Pat. No. 4,410,512.

Other suitable peptides include hexapeptides such as the growth hormone releasing peptide (GHRP) His-D-Trp-Ala-Trp-D-Phe-Lys-$NH_2$, (Momany, U.S. Pat. No. 4,411,890, the disclosure of which is herein incorporated by reference in its entirety). This may usefully be included in an amount up to about 250 mg/g of the hydrophilic phase or from 0.1 to 25 mg/kg of the formulation.

Suitable larger polypeptides and proteins for use in the controlled release formulations of the present invention include insulin, calcitonin, elcatonin, calcitoningene related peptide and porcine somatostatin as well as analogs and homologs thereof. Other suitable larger polypeptides include those disclosed by Pierschbacher et al, U.S. Pat. No. 4,589, 881 (>30 residues); Bittle et al, U.S. Pat. No. 4,544,500 (20–30 residues); and Dimarchi et al, EP 0204480 (>34 residues).

Other type of compounds useful in the present invention include analogs or homologs of LHRH which display potent LH releasing activity or inhibit the activity of LHRH; analogs or homologs of HP5 which possesses hematopoetic activity; analogs or homologs of endothelin which possess hypotensive activity; analogs or homologs of enkephalin which have antinociceptive activity; analogs or homologs of chlorecystokinin; analogs or homologs of cyclosporin A which have immunosuppressive activity; analogs or homologs of atrial natriuretic factor; peptidergic antineoplastic agents; analogs or homologs of gastrin releasing peptide; analogs or homologs of somatostatin; gastrin antagonists; bradykinin antagonists; neurotensin antagonists; bombesin antagonists; oxytocin agonists and antagonists; vasopressin agonists and antagonists; hirudin analogs and homologs; analogs and homologs of the cytoprotective peptidecyclolinopeptide; alpha MSH analogs; analogs, and homologs of MSH releasing factor (Pro-Leu-Gly-$NH_2$); peptides which inhibit collagenase; peptides which inhibit elastase, peptides which inhibit renin; peptides which inhibit HIV protease; peptides which inhibit angiotensin converting enzyme; peptides which inhibit chymases and tryptases and peptides which inhibit blood coagulation enzymes.

Other suitable drugs include non-peptide therapeutic agents such as antibiotics, antimicrobial agents, antineoplastic agents, cardiovascular and renal agents, such as captopril, anti-inflammatory, immunosuppressive and immunostimulatory agents and CNS agents.

Preferably, the water-soluble drug is metformin or salt thereof as described above.

The biphasic controlled release formulation of the present invention can be administered to various mammalian species, such as dogs, cats, humans, etc., in need of such treatment.

The biphasic controlled release system of the invention can be incorporated in a conventional systemic dosage form, such as a tablet or capsule. The above dosage forms may also include the necessary physiologically acceptable carrier material, excipient, lubricant, buffer, antibacterial, bulking agent (such as mannitol), anti-oxidants (ascorbic acid or sodium bisulfite) or the like.

The dose administered must be carefully adjusted according to the age, weight, and condition of the patient, as well as the route of administration, dosage form and regimen, and the desired result. In general, the dosage forms of formulation containing metformin or salt thereof (whether by itself or with another antihyperglycemic agent and/or a hypolipidemic agent) described above may be administered in amounts as described for metformin hydrochloride (Bristol-Myers Squibb Company's Glucophage®) as set out in the Physician's Desk Reference.

The combination of the metformin or salt thereof and the other antihyperglycemic agent and/or hypolipidemic agent may be formulated separately or, where possible, in a single formulation employing conventional formulation procedures.

The various formulations of the invention may optionally include one or more fillers or excipients in an amount within the range of from about 0 to about 90% by weight and preferably from about 1 to about 80% by weight such as lactose, sugar, corn starch, modified corn starch, mannitol, sorbitol, inorganic salts such as calcium carbonate and/or cellulose derivatives such as wood cellulose and microcrystalline cellulose (also referred to as a compression aid).

One or more binders may be present in addition to or in lieu of the fillers in an amount within the range of from about 0 to about 35% and preferably from about 0.5 to about 30% by weight of the composition. Examples of such binders which are suitable for use herein include polyvinylpyrrolidone (molecular weight ranging from about 5000 to about 80,000 and preferably about 40,000), lactose, starches such as corn starch, modified corn starch, sugars, gum acacia and the like as well as a wax binder in finely powdered form (less than 500 microns) such as carnauba wax, paraffin, spermaceti, polyethylenes or microcrystalline wax.

Where the composition is to be in the form of a tablet, it will include one or more tableting lubricants in an amount within the range of from about 0.2 to about 8% and preferably from about 0.5 to about 2% by weight of the composition, such as magnesium stearate, stearic acid, palmitic acid, calcium stearate, talc, carnauba wax and the like. Other conventional ingredients which may optionally be present include preservatives, stabilizers, anti-adherents or silica flow conditioners or glidants, such as Syloid brand silicon dioxide as well as FD&C colors.

Tablets of the invention may also optionally include an optional coating layer which may comprise from 0 to about 15% by weight of the tablet composition. The coating layer which is applied over the outer solid phase containing particles of inner solid phase embedded therein may comprise any conventional coating formulations and will include one or more film-formers or binders, such as a hydrophilic polymer like hydroxypropylmethylcellulose, and/or a hydrophobic polymer like methacrylic acid esters neutral polymer, ethyl cellulose, cellulose acetate, polyvinyl alcohol-maleic anhydride copolymers, β-pinene polymers, glyceryl esters of wood resins and the like and one or more plasticizers, such as triethyl citrate, diethyl phthalate, propylene glycol, glycerin, butyl phthalate, castor oil and the like. Both core tablets as well as coating formulations may contain aluminum lakes to provide color.

The film formers are applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1-trichloroethane.

Where a color is employed, the color will be applied together with the film former, plasticizer and solvent compositions.

It will be recognized by one of skill in the art that the amount of drug required for therapeutic effect on administration will, of course, vary with the agent chosen, the nature and severity of the condition and the animal undergoing treatment, and is ultimately at the discretion of the physician. Furthermore, the optimal quantity and spacing of individual dosages of a drug will be determined by the nature and extent of the condition being treated, the form, route and site of administration, the particular patient being treated and that such optima can be determined by conventional techniques. It will also be appreciated that the optimal course of treatment, this is, the number of doses given, can be ascertained by those skilled in the art using conventional course of treatment determination tests.

As indicated, the preferred highly water-soluble drug will be metformin or a salt thereof, which will be employed in a dosage range from about 2 to about 43 mg/kg, preferably about 3 to about 36 mg/kg and more preferably from about 4.5 to about 30 mg/kg (or from about 150 to about 3000 mg, preferably from about 250 to about 2500 mg) on a regimen in single daily dose or 2 to 4 divided daily doses, 1 to 4 times daily.

Where metformin is to be administered once daily, metformin will be employed in an amount of at least one gram, preferably from about one to about 3 grams and more preferably from about 1 to about 2.5 grams, in one, two or more tablets and/or one, two or more capsules.

The biphasic controlled release formulation of the invention may be prepared in accordance with the following method of the invention.

A mixture of medicament (preferably metformin HCl) and hydrophilic polymer and/or hydrophobic polymer and/or other hydrophobic material are dispersed/dissolved in a suitable solvent such as water or an inert organic solvent such as ethanol, isopropanol, acetone or dichloromethane or appropriate mixtures of two or more thereof, to produce a substantially uniform granulation. The granulation is dried and passed through a 0.5 to 2 mm aperture screen to break down agglomerates.

The resulting dry granules are blended with hydrophilic polymer and/or hydrophobic polymer and/or other hydrophobic material. The resulting mix usually with lubricant is pressed into tablets or filled into capsules.

The finished dosage form is either a compressed tablet or a hard gelatin capsule, preferably a tablet. The tablet may be optionally film coated. The total amount of drug per dosage unit would be such as to offer a dosage form of convenient size for patients, but following ingestion would remain (or swell to, by hydration of the polymers used in the fabrication of the tablet) a size that does not easily pass through the pylorus (15 mm or greater) when taken with a meal. As the tablet swells up to approximately three times its dry size following hydration, drug loads of up to 750 mg and more are possible, dependent upon the actual characteristics of the individual drug. Gradual erosion of the polymers of the formulation over a period of up to 15 hours ensures that the dosage form does not produce a gastrointestinal obstruction.

Useful metformin formulations of the invention show the following drug release characteristic when tested in vitro.

| Time (hours) | % released |
|---|---|
| 1 | 28–39 |
| 2 | 43–57 |
| 3 | 53–70 |
| 5 | 70–88 |
| 7 | 80–98 |
| 10 | >85 |

In addition, in accordance with the present invention, the controlled release metformin formulation of the invention (relative to the rapid-release marketed Glucophage® tablets) reduces maximum attained plasma-metformin concentration (Cmax) by at least about 15% (preferably from about 15 to about 30%), and increases time to reach maximum metformin plasma concentration (Tmax) by at least about 30% (preferably from about 30 to about 100%), while having an insignificant effect on area under the plasma-metformin concentration time curve (AUC) and % urinary recovery (UR) of the dose of metformin. Thus, the controlled-release metformin formulation of the invention can be employed for once daily dosing of metformin in the treatment of diabetes.

The following Examples represent preferred embodiments of the invention.

EXAMPLE 1

Biphasic Metformin HCl Formulation 25 g of ethylcellulose N10 NF was dissolved/dispersed in 100 ml of 95% ethanol. This dispersion was gradually added to 500 g of metformin hydrochloride in a planetary mixer to produce a uniform damp granulation. The granulation was dried at 55° C. for one hour and passed through a 0.8 mm aperture screen to break down agglomerates. The metformin-ethylcellulose granules (541 g) were blended with 351.5 g of hydroxypropylmethylcellulose 2208 USP (100,000 cps grade), 10 g of hydroxypropylmethylcellulose 2910 USP (5 cps grade) and 100.5 g of microcrystalline cellulose in a planetary mixer for 10 minutes. Finally this mix was lubricated with 1% w/w magnesium stearate and compressed into capsule shaped tablets, each containing 500 mg metformin hydrochloride. When subjected to in vitro drug release testing, the following results were obtained.

| Time (hours) | % metformin released |
|---|---|
| 1 | 38.1 |
| 2 | 56.3 |
| 3 | 69.5 |
| 4 | 79.7 |
| 5 | 87.4 |
| 6 | 93.1 |
| 7 | 97.7 |
| 8 | 100 |

EXAMPLE 2

Biphasic Metformin HCl Formulation 51 g of sodium carboxymethylcellulose (Blanose 7HF) was mixed with 500 g of metformin hydrochloride and granulated with 95% ethanol in a small planetary mixer. The damp granulation was passed through a 2 mm aperture screen and then dried in an oven at 55° C. for one hour. The dried granulation (530 g) was blended with 344 g of hydroxypropylmethylcellulose 2208 USP (100,000 cps grade), 9.5 g of hydroxypropylmethylcellulose 2910 USP (5 cps grade) and 100 g of microcrystalline cellulose in a planetary mixer for 10 minutes. This blend was lubricated with 1% w/w magnesium stearate and compressed into capsule shaped tablets, each containing 500 mg metformin hydrochloride. When the tablets were subjected to in vitro release testing the following results were obtained.

| Time (hours) | % metformin released |
|---|---|
| 1 | 35.3 |
| 2 | 51.4 |
| 3 | 62.6 |
| 4 | 70.7 |
| 5 | 76.7 |
| 6 | 82.1 |
| 7 | 85.3 |
| 8 | 88.5 |
| 10 | 92.6 |

EXAMPLE 3

Biphasic Metformin HCl Formulation

Metformin hydrochloride (502.5 g) was mixed with sodium carboxymethylcellulose (Blanose 7HF) (50 g) for five minutes in a small planetary mixer and sufficient purified water added with continued mixing to produce a damp granular mass. The wet granulation was dried at 60° C. for 1 hour and then size reduced in a hammer mill. The granulation was dry blended with a mixture prepared from 358 g of hydroxypropylmethylcellulose 2208 USP (100,000 cps grade), 10 g of hydroxypropylmethylcellulose 2910 USP (5 cps grade) and 102 g of microcrystalline cellulose in a planetary mixer for 10 minutes. Finally this mix was lubricated by mixing with 1% w/w magnesium stearate and compressed into capsule shaped tablets, each containing 0.5 g of metformin hydrochloride. When tested for in vitro release of metformin the following results were obtained.

| Time (hours) | % metformin released |
|---|---|
| 1 | 33.1 |
| 2 | 47.6 |
| 3 | 57.5 |
| 4 | 65.1 |
| 6 | 76.5 |
| 8 | 84.3 |
| 10 | 88.6 |

EXAMPLE 4

Biphasic Metformin HCl Formulation 200 g of glycerol monostearate was heated to 70° C. in a high shear mixer bowl and 199 g of metformin hydrochloride was added and the mixer operated with impeller at 90 rpm and chopper at 215 rpm for 5 minutes. A further 796 g of metformin hydrochloride was added gradually with continued mixing, maintaining thee granulation at 70° C. and with an increase in chopper speed first to 500 rpm for 13 minutes, then to 1000 rpm for a further 3 minutes. The bowl was then cooled to 60° C., the impeller speed was reduced to 20 rpm and the chopper speed increased to 2000 rpm. Cooling was continued with adjustment in impeller and chopper speed to eventually provide a cooled solid granulation. The cooled granulation was deagglomerated by passing through a 0.8 mm screen.

540.5 g of the granulation was blended with 350 g of hydroxypropylmethylcellulose 2208 USP (100,000 cps grade), 10 g hydroxypropylmethylcellulose 2910 USP (5 cps grade) and 100 g of microcrystalline cellulose in a planetary mixer for 10 minutes. The blend was lubricated by blending with 1% w/w magnesium stearate and then compressed into capsule shaped tablets each containing 500 mg metformin hydrochloride. When tested for in vitro release of metformin, the following results were obtained.

| Time (hours) | % metformin released |
|---|---|
| 1 | 32.4 |
| 2 | 45.7 |
| 3 | 55.8 |
| 4 | 63.7 |
| 5 | 70.3 |
| 6 | 75.7 |
| 8 | 83.3 |
| 10 | 88.6 |

EXAMPLE 5

Biphasic Metformin HCl Formulation

Tablets containing 500 mg metformin hydrochloride prepared according to Example 3 or Glucophage brand (or rapid release) metformin hydrochloride 500 mg tablets was dosed (2×500 mg tablets) to 24 patients immediately after dinner. Blood samples were taken at 0, 0.5, 1, 2, 3, 4, 5, 6, 7, 8, 10, 12, 14, 16, 20, 24 hours and analyzed for metformin. The mean plasma profile demonstrated useful modification of drug release in vivo relative to the immediate release formulation and with no impact on bioavailability in contrast to other metformin extended release formulations reported in the literature.

Interpatient variability in pharmacokinetic parameters was acceptable as illustrated by the mean parameters (%CV) given in the table below:

| Formulation | Cmax (ng/ml) | AUC (inf) (ng.hr/ml) | Tmax*(hr) | % UR (Urinary Recovery) |
|---|---|---|---|---|
| Glucophage | 1226(16) | 10128(14) | 3.5(1,5) | 43.3(20) |
| Example 3 | 978(13) | 10483(21) | 5(4,8) | 42.7(18) |

*median (min., max.)

For the Example 3 once a day tablet formulation of the invention (relative to the rapid release Gilucophage® tablet), the time required to reach maximum metformin plasma concentration (Tmax) is increased by an average of about 40%, and the maximum attained plasma metformin concentration (Cmax) is reduced by an average of about 20%, yet the area under plasma-metformin concentration time curve (AUC) and the % urinary recovery (UR) of the dose of metformin are not significantly different from that found with rapid-release Glucophage®. This means that overall patient exposure to metformin (in both the Example 3 formulation and the Glucophage®) is equivalent.

Thus, in view of the above results, it is seen that the pharmacokinetic parameters found for the Example 3 tablet formulation of the invention indicate that the Example 3 tablet formulation can be employed for once daily dosing of metformin in the treatment of diabetes.

The new formulations of the invention thus represent a significant advance in the once-a-day administration of metformin hydrochloride to humans in the treatment of diabetes.

EXAMPLE 6

Preparation of Metformin (2:1) Fumarate

Metformin base (8.71 moles) (prepared from the hydrochloride salt via an ion-exchange column) was dissolved in methanol/$H_2O$ [5:1]. With stirring, a solution of fumaric acid (4.05 moles) in ethanol was added over a period of one hour under a nitrogen atmosphere at ambient temperature (~20° C.). Crystallization began to occur immediately. After stirring the slurry for one hour at ambient temperature, the product was filtered off, washed with ethanol and dried under vacuum to afford the metformin (2:1) fumarate salt as a free-flowing white crystalline solid in 72 M% yield and melting point of 247–249° C.

The resulting metformin (2:1) fumarate slat had a solubility in water (mg/ml) of 140, a hygroscopicity measured at 95% relative humidity/25° C. of less than 7% moisture uptake at 6 hours, and a low compaction susceptibility.

The so-formed metformin salt is used to prepare a biphasic controlled release formulation employing the procedure of Example 3.

EXAMPLE 7

Preparation of Metformin (2:1) Succinate

Metformin base (8.95 moles) (prepared from the hydrochloride salt via an ion-exchange column) was dissolved in methanol/$H_2O$ [5:1]. With stirring, a solution of succinic acid (4.42 moles) in ethanol was added over one hour under a nitrogen atmosphere at ambient temperature (~20°). Crystallization of the salt commenced shortly after addition of the succinic acid solution. After stirring the slurry for an hour at ambient temperature, the product was filtered off, washed with ethanol and dried under vacuum to form the metformin (2:1) succinate salt as a free flowing white crystalline solid in 89 M% yield and melting point of 246–247° C.

The resulting metformin (2:1) succinate salt had a solubility in water (mg/ml) of 95, a hygroscopicity measured at 95% relative humidity/25° C. of less than 1% moisture uptake at 30 minutes, and a low compaction susceptibility.

The so-formed metformin salt is used to prepare a biphasic controlled release formulation employing the procedure of Example 3.

The metformin formulations described in the aforesaid Examples may be administered once daily as described above, in one, two or more tablets and/or capsules to provide optimal therapeutic control.

REFERENCES

1. Vidon, N., Chaussade, S., Noel, M., Franchisseur, C., Huchet, B., Bernier, J. J. (1988), Diabetes Research and Clinical Practice, 4, 223–239.
2. Pentikainen, P. J. (1986), International Journal of Clinical Pharmacology, Therapy and Toxicology, 24, 213–220.
2A. Noel, D. S. (1980), Kinetic study of normal and sustained release dosage forms of metformin in normal subjects, Journal of International Biomedical Information and Data, 1980, pp. 9 to 20.

2B. Karttunen et al (1983), The pharmacokinetics of metformin: a comparison of the properties of a rapid-release and a sustained-release preparation, Int. J. Clin. Pharmacology, Therapy and Toxicology, Vol. 21, No. 1, pp. 31–36.

3. Watanabe, S., Kayano, M., Ishino, Y., Miyao, K. (1976), U.S. Pat. No. 3,976,764.
4. Sheth, P., Tossounian, J. L. (1979), U.S. Pat. No. 4,140,755.
5. Sheth, P., Tossounian, J. L. (1978), U.S. Pat. No. 4,126,672.
6. Sheth, P., Tossounian, J. L. (1979), U.S. Pat. No. 4,167,558.
7. Dennis, A. B., Lee, K., Timmins, P. (1992), U.S. Pat. No. 5,169,638.
8. Franz, M. R., Oth, M. P. (1993), U.S. Pat. No. 5,232,704.
9. Ishikawa, M., Miyaka, Y., Watanabe, S. (1989), U.S. Pat. No. 4,844,905.
10. Davis, S. S., Stockwell, A. F., Taylor, J. J., Hardy, J. G., Whalley, D. R., Wilson, C. G., Bechgaard, H., Christensen, F. N. (1986) Pharm. Res., 3, 208–213.
11. Timmermans, J., Moes, A. (1994), J. Pharm. Sci., 83, 18–24.
12. Caldwell, L. J., Gardener, C. R., Cargill, R. C. (1988), U.S. Pat. No. 4,767,627.
13. Urquart, J., Theeuwes, F. (1984), U.S. Pat. No. 4,434,153.
14. Shell, J. W. (1990), U.S. Pat. No. 5,007,790.
15. Shell, J. W. (1993), World Patent WO 9318755.
16. Shell, J. W. (1996), U.S. Pat. No. 5,582,837.
17. Fisher, M. C., Morella, A. M. (1994), European Patent 609961.
18. Hansraj, B. R., Bashir, R. H. (1992), European Patent 502642.
19. Rollet, M. (1987), French Patent 2594693.
20. Howard, S. A., Kotwal, P. M. (1997) U. S. Pat. No. 5,645,858.
21. Macrae, R. J., Smith J. S. (1997), World Patent WO 9718814.
22. Belenduik, G. W., McCarty, J. A., Rudnic, E. M. (1996), U.S. Pat. No. 5,484,608.
23. Bhatti, G. K., Edgren, D. E., Hatamkhani, Z., Wong, P. S., Wong, P. S. L. (1994), World Patent WO 9427589.
24. Palepu, N. R., Venkatesh, G. M., (1997) European Patent 701436.

What is claimed is:

1. A method for treating diabetes comprising administering once daily to a mammalian patient in need of treatment a therapeutically effective amount of a pharmaceutical formulation comprising (1) an inner solid particulate phase, and (2) an outer solid continuous phase in which particles of said inner solid particulate phase are dispersed and embedded, the particles of said inner solid particulate phase comprising (a) a pharmaceutical having a high water solubility selected from metformin or a pharmaceutically acceptable salt thereof; and (b) an extended release material, and said outer solid continuous phase comprising an extended release material, wherein the total extended release material content in both said inner solid particulate phase and said outer continuous phase is within the range from about 25 to about 75% by weight of the pharmaceutical formulation.

2. The method for treating diabetes as defined in claim 1 wherein said pharmaceutical formulation is a biphasic heterogeneous controlled release formulation which is designed to release pharmaceutical from the particles forming said inner solid particulate phase through said outer solid continuous phase into the upper gastrointestinal tract.

3. The method for treating diabetes as defined in claim 1 wherein the total extended release material content in both said inner solid particulate phase and said outer solid continuous phase is within the range from about 30 to about 65% by weight of the pharmaceutical formulation.

4. The method for treating diabetes as defined in claim 1 wherein said pharmaceutical is metformin hydrochloride.

5. The method for treating diabetes as defined in claim 1 wherein said extended release material present in said inner solid particulate phase is different from the extended release material present in said outer solid continuous phase.

6. The method for treating diabetes as defined in claim 1 wherein the total extended release material content in both said inner solid particulate phase and said outer solid continuous phase is within the range from about 35 to about 60% by weight of the pharmaceutical formulation.

7. The method for treating diabetes as defined in claim 3 wherein said inner solid particulate phase contains from about 5 to about 95% extended release material based on the weight of said inner solid particulate phase, and the outer solid continuous phase contains from about 40 to about 100% extended release material based on the weight of said outer solid continuous phase.

8. The method for treating diabetes as defined in claim 1 wherein said formulation when ingested by a human reduces maximum attained plasma-metformin concentration (Cmax) by at least about 15% (relative to marketed rapid-release metformin formulations), and increases time to reach maximum metformin-plasma concentration (Tmax) by at least about 30% (relative to marketed rapid-release metformin formulations), while having an insignificant effect on area under the plasma-metformin concentration time curve (AUC) and % urinary recovery (UR) of the dose of metformin (relative to marketed rapid-release metformin formulations).

9. The method for treating diabetes as defined in claim 1 wherein said formulation contains metformin in a therapeutically effective amount which allows a patient a dosing regimen of at least one gram metformin, or a pharmaceutically acceptable salt thereof, once daily, while providing effective control of plasma glucose.

10. The method for treating diabetes as defined in claim 9 wherein said formulation provides for a dosing regimen of from about 1 to about 3 grams once daily.

11. The method for treating diabetes as defined in claim 9 wherein said inner solid particulate phase is in the form of discrete individual particles or granules and said outer solid continuous phase is a substantially continuous matrix having individual particles forming said inner solid particulate phase embedded therein and dispersed throughout.

12. The method for treating diabetes as defined in claim 9 wherein said formulation when ingested by a human reduces maximum attained plasma-metformin concentration (Cmax) by at least about 15% (relative to marketed rapid-release metformin formulations), and increases time to reach maximum metformin-plasma concentration (Tmax) by at least about 30% (relative to marketed rapid-release metformin formulations), while having an insignificant effect on area under the plasma-metformin concentration time curve (AUC) and % urinary recovery (UR) of the dose of metformin (relative to marketed rapid-release metformin formulations).

13. The method for treating diabetes as defined in claim 1 wherein said metformin is metformin (2:1) fumarate.

14. The method of treating diabetes as defined in claim 1 wherein said inner solid particulate phase of said formulation is present in a weight ratio to said outer solid continuous phase within the range from about 0.5:1 to about 4:1.

15. The method of treating diabetes as defined in claim 1 wherein said pharmaceutical is present in said inner solid particulate phase of said formulation in an amount within the range from about 10 to about 98% weight of said inner solid particulate phase.

16. The method for treating diabetes as defined in claim 1 wherein said extended release material present in said inner solid particulate phase of said formulation comprises one or more hydrophilic polymers, and/or one or more hydrophobic polymers and/or one or more other hydrophobic materials; and said extended release material in said outer solid continuous phase of said formulation comprises one or more hydrophilic polymers, and/or one or more hydrophobic polymers and/or one or more other hydrophobic materials.

17. The method for treating diabetes as defined in claim 16 wherein said extended release material present in said inner solid particulate phase comprises one or more ionic polymers and said extended release material present in said outer solid continuous phase comprises one or more non-ionic polymers.

18. The method for treating diabetes as defined in claim 17 wherein said ionic polymer comprises sodium alginate, carbomer, calcium carboxymethylcellulose or sodium carboxymethylcellulose, and said non-ionic polymer comprises hydroxypropylmethylcellulose 2208 USP, viscosity grade ranging from about 4000 to about 100,000 cps and/or hydroxypropylmethyl cellulose 2910 USP viscosity grade ranging from about 3 to about 150 cps.

19. The method for treating diabetes as defined in claim 1 wherein said inner solid particulate phase of said pharmaceutical formulation has a mean particle size within the range from about 30 µm to about 0.8 mm.

20. The method for treating diabetes as defined in claim 1 wherein said inner solid particulate phase of said pharmaceutical formulation comprises metformin, metformin hydrochloride, metformin succinate (2:1) salt or metformin fumarate (2:1) salt, and ethyl cellulose and/or sodium carboxymethyl cellulose and/or glycerylmonostearate and said outer solid continuous phase comprises hydroxypropylmethylcellulose 2208 USP (100,000 cps), and/or hydroxypropylmethylcellulose 2910 USP (5 cps) and/or microcrystalline cellulose.

21. The method for treating diabetes as defined in claim 1 wherein said pharmaceutical formulation further comprises another antihyperglycemic agent and/or hypolipidemic agent.

22. The method for treating diabetes as defined in claim 21 wherein said other antihyperglycemic agent is a sulfonyl urea, a glucosidase inhibitor, a thiazolidenedione, insulin, or glucogon-like peptide-1.

23. The method for treating diabetes as defined in claim 21 wherein said other antihyperglycemic agent is glyburide, glipizide, pioglitazone or rosiglitazone.

24. The method for treating diabetes as defined in claim 21 wherein said hypolipidemic agent is an MTP inhibitor, a squalene synthetase inhibitor, and HMG CoA reductase inhibitor, a fibric acid derivative, an ACAT inhibitor, a cholesterol absorption inhibitor, an ileal $Na^{+/}$bile cotransporter inhibitor, a bile acid sequestrant and/or nicotinic acid or a derivative thereof.

25. The method for treating diabetes as defined in claim 21 wherein said hypolipidelmic agent is pravastatin, simvastatin, lovastatin, atorvastatin, fluvastatin or cerivastatin.

26. The method for treating diabetes as defined in claim 21 wherein said metformin is present in a weight ratio to said other antihyperglycemic agent or hypolipidemic agent within the range from about 0.01:1 to about 300:1.

27. A method for treating diabetes comprising administering a pharmaceutical formulation comprising (1) an inner solid particulate phase, and (2) an outer solid continuous phase in which particles of said inner solid particulate phase are dispersed and embedded, the particles of said inner solid particulate phase comprising (a) metformin or a pharmaceutically acceptable salt thereof; and (b) an extended release material, and said outer solid continuous phase comprising an extended release material, wherein said extended release material present in said inner solid particulate phase is different from the extended release material present in said outer solid continuous phase and wherein the total extended release material content in both said inner solid particulate phase and said outer solid continuous phase is within the range from about 25 to about 75% by weight of the pharmaceutical formulation.

28. The method for treating diabetes as defined in claim 27 comprising administering said pharmaceutical formulation which is a biphasic heterogeneous controlled release formulation which is designed to release metformin from the particles forming said inner solid particulate phase through said outer solid continuous phase into the upper gastrointestinal tract.

29. The method for treating diabetes as defined in claim 27 wherein the metformin is metformin hydrochloride.

30. The method for treating diabetes as defined in claim 27 wherein the total extended release material content in both said inner solid particulate phase and said outer solid continuous phase is within the range from about 30 to about 65% by weight of the pharmaceutical formulation.

31. The method for treating diabetes as defined in claim 27 wherein said inner solid particulate phase contains from about 5 to about 95% extended release material based on the weight of said inner solid particulate phase.

32. The method for treating diabetes as defined in claim 27 wherein said outer solid continuous phase contains from about 40 to about 100% extended release material based on the weight of said outer solid continuous phase.

33. The method for treating diabetes as defined in claim 27 wherein said inner solid particulate phase is in the form of discrete individual particles or granules and said outer solid continuous phase is a substantially continuous matrix having individual particles forming said inner solid particulate phase embedded therein and dispersed throughout.

34. The method for treating diabetes as defined in claim 27 wherein said metformin is metformin (2:1) fumarate.

35. The method of treating diabetes as defined in claim 27 wherein said inner solid particulate phase is present in a weight ratio to said outer solid continuous phase within the range from about 0.5:1, to about 4:1.

36. The method of treating diabetes as defined in claim 27 wherein said metformin is present in said inner solid particulate phase in an amount within the range from about 10 to about 98% by weight of the inner solid particulate phase.

37. The method of treating diabetes as defined in claim 27 wherein the extended release material present in said inner solid particulate phase comprises one or more hydrophilic polymers, and/or one or more hydrophobic polymers and/or one or more other hydrophobic materials; and the extended release material in said outer solid continuous phase comprises one or more hydrophilic polymers, and/or one or more hydrophobic polymers and/or one or more other hydrophobic materials.

38. The method of treating diabetes as defined in claim 37 wherein the extended release material present in the inner solid particulate phase comprises one or more ionic polymers and the extended release material present in said outer solid continuous phase comprises one or more non-ionic polymers.

39. The method of treating diabetes as defined in claim 38 wherein said ionic polymer comprises sodium alginate, carbomer, calcium carboxymethylcellulose or sodium carboxymethylcellulose, and said non-ionic polymer comprises hydroxypropylmethylcellulose 2208 USP, viscosity grade ranging from about 4000 to about 100,000 cps and/or hydroxypropylmethyl cellulose 2910 USP viscosity grade ranging from about 3 to about 150 cps.

40. The method of treating diabetes as defined in claim 27 wherein said inner solid particulate phase has a mean particle size within the range from about 30 mm to about 0.8 mm.

41. The method of treating diabetes as defined in claim 27 wherein said inner solid particulate phase comprises metformin, metformin hydrochloride metformin succinate (2:1) salt or metformin fumarate (2:1) salt, and ethyl cellulose and/or sodium carboxymethyl cellulose and/or glycerylmonostearate and said outer solid continuous phase comprises hydroxypropylmethylcellulose 2208 USP (100,000 cps), and/or hydroxypropylmethylcellulose 2910 USP (5 cps) and/or microcrystalline cellulose.

42. The method of treating diabetes as defined in claim 27 wherein said pharmaceutical formulation further comprises another antihyperglycemic agent and/or a hypolipidemic agent.

43. The method of treating diabetes as defined in claim 42 wherein said other antihyperglycemic agent is a sulfonyl urea, a glucosidase inhibitor, a thiazolidenedione, insulin, or glucogon-like peptide-1.

44. The method of treating diabetes as defined in claim 42 wherein the other antihyperglycemic agent is glyburide, glipizide, pioglitazone or rosiglitazone.

45. The method of treating diabetes as defined in claim 42 wherein said hypolipidemic agent is an MTP inhibitor, a squalene synthetase inhibitor, an HMG CoA reductase inhibitor, a fibric acid derivative, an ACAT inhibitor, a cholesterol absorption inhibitor, an ileal $Na^{+}$/bile cotransporter inhibitor, a bile acid sequestrant and/or nicotinic acid or a derivative thereof.

46. The method of treating diabetes as defined in claim 42 wherein said hypolipidemic agent is pravastatin, simvastatin, lovastatin, atorvastatin, fluvastatin or cerivastatin.

47. The method of treating diabetes as defined in claim 27 wherein said formulation when ingested by a human reduces maximum attained plasma-metformin concentration (Cmax) by at least about 15% (relative to marketed rapid-release metformin formulations), and increases time to reach maximum metformin-plasma concentration (Tmax) by at least about 30% (relative to marketed rapid-release metformin formulations), while having an insignificant effect on area under the plasma-metformin concentration time curve (AUC) and % urinary recovery (UR) of the dose of metformin (relative to marketed rapid-release metformin formulations).

48. A method of lowering insulin resistance which comprises administering once daily to a mammalian patient in need of such treatment a therapeutically effective amount of a pharmaceutical formulation comprising (1) an inner solid particulate phase, and (2) an outer solid continuous phase in which particles of said inner solid particulate phase are dispersed and embedded, the particles of said inner solid particulate phase comprising (a) a pharmaceutical having a high water solubility selected from metformin or a pharmaceutically acceptable salt thereof; and (b) an extended release material, and said outer solid continuous phase comprising an extended release material, wherein the total extended release material content in both said inner solid particulate phase and said outer continuous phase is within the range from about 25 to about 75% by weight of the pharmaceutical formulation.

49. The method of lowering insulin resistance as defined in claim 48 wherein the total extended release material content in both said inner solid particulate phase and said outer solid continuous phase is within the range from about 30 to about 65% by weight of the pharmaceutical formulation.

50. The method of lowering insulin resistance as defined in claim 48 wherein the total extended release material content in both said inner solid particulate phase and said outer solid continuous phase is within the range from about 35 to about 60% by weight of the pharmaceutical formulation.

51. The method of lowering insulin resistance as defined in claim 48 wherein said formulation when ingested by a human reduces maximum attained plasma-metformin concentration (Cmax) by at least about 15% (relative to marketed rapid-release metformin formulations), and increases time to reach maximum metformin-plasma concentration (Tmax) by at least about 30% (relative to marketed rapid-release metformin formulations), while having an insignificant effect on area under the plasma-metformin concentration time curve (AUC) and % urinary recovery (UR) of the dose of metformin (relative to marketed rapid-release metformin formulations).

52. The method of lowering insulin resistance as defined in claim 48 wherein said extended release material present in said inner solid particulate phase comprises one or more hydrophilic polymers, and/or one or more hydrophobic polymers and/or one or more other hydrophobic materials; and the extended release material in said outer solid continuous phase comprises one or more hydrophilic polymers, and/or one or more hydrophobic polymers and/or one or more other hydrophobic materials.

53. The method of lowering insulin resistance as defined in claim 48 wherein said inner solid particulate phase of said pharmaceutical formulation comprises metformin, metformin hydrochloride, metformin succinate (2:1) salt or metformin fumarate (2:1) salt, and ethyl cellulose and/or sodium carboxymethyl cellulose and/or glycerylmonostearate and said outer solid continuous phase comprises hydroxypropylmethylcellulose 2208 USP (100,000 cps), and/or hydroxypropylmethylcellulose 2910 USP (5 cps) and/or microcrystalline cellulose.

54. The method of lowering insulin resistance as defined in claim 48 wherein said pharmaceutical formulation further comprises another antihyperglycemic agent and/or hypolipidemic agent.

55. A method of lowering insulin resistance which comprises administering to a mammalian patient in need of such treatment a therapeutically effective amount of a pharmaceutical formulation comprising (1) an inner solid particulate phase, and (2) an outer solid continuous phase in which particles of said inner solid particulate phase are dispersed and embedded, the particles of the inner solid particulate phase comprising (a) metformin or a pharmaceutically acceptable salt thereof; and (b) an extended release material, and said outer solid continuous phase comprising an extended release material, wherein the extended release material present in said inner solid particulate phase is different from the extended release material present in said outer solid continuous phase and wherein the total extended release material content in both said inner solid particulate phase and said outer solid continuous phase is within the range from about 25 to about 75% by weight of the pharmaceutical formulation.

56. The method of lowering insulin resistance as defined in claim 55 wherein the total extended release material content in both said inner solid particulate phase and said out solid continuous phase is within the range from about 30 to about 65% by weight of the pharmaceutical formulation.

57. The method of lowering insulin resistance as defined in claim 55 wherein the extended release material present in said inner solid particulate phase comprises one or more hydrophilic polymers, and/or one or more hydrophobic polymers and/or one or more other hydrophobic materials; and the extended release material in said outer solid continuous phase comprises one or more hydrophilic polymers, and/or one or more hydrophobic polymers and/or one or more other hydrophobic materials.

58. The method of lowering insulin resistance as defined in claim 55 wherein said inner solid particulate phase comprises metformin, metformin hydrochloride, metformin succinate (2:1) salt or metformin fumarate (2:1) salt, and ethyl cellulose and/or sodium carboxymethyl cellulose and/or glycerylmonostearate and said outer solid continuous phase comprises hydroxypropylmethylcellulose 2208 USP (100,000 cps), and/or hydroxypropylmethylcellulose 2910 USP (5 cps) and/or microcrystalline cellulose.

59. The method of lowering insulin resistance as defined in claim 55 wherein said pharmaceutical formulation further comprises another antihyperglycemic agent and/or hypolipidemic agent.

60. The method of lowering insulin resistance as defined in claim 55 wherein said formulation when ingested by a human reduces maximum attained plasma-metformin concentration (Cmax) by at least about 15% (relative to marketed rapid-release metformin formulations), and increases time to reach maximum metformin-plasma concentration (Tmax) by at least about 30% (relative to marketed rapid-release metformin formulations), while having an insignificant effect on area under the plasma-metformin concentration time curve (AUC) and % urinary recovery (UR) of the dose of metformin (relative to marketed rapid-release metformin formulations).

* * * * *

(12) EX PARTE REEXAMINATION CERTIFICATE (9149th)
United States Patent
Timmins et al.

(10) Number: US 6,660,300 C1
(45) Certificate Issued: Jul. 24, 2012

(54) METHOD OF USE OF A BIPHASIC CONTROLLED RELEASE DELIVERY SYSTEM FOR HIGH SOLUBILITY PHARMACEUTICALS AND METHOD

(75) Inventors: Peter Timmins, Irby (GB); Andrew B. Dennis, Barnston (GB); Kiren A. Vyas, Canterbury (GB)

(73) Assignee: Bristol-Myers Squibb Company, Princeton, NJ (US)

Reexamination Request:
No. 90/011,872, Aug. 21, 2011

Reexamination Certificate for:
Patent No.: 6,660,300
Issued: Dec. 9, 2003
Appl. No.: 10/224,945
Filed: Aug. 21, 2002

Related U.S. Application Data

(60) Division of application No. 09/398,107, filed on Sep. 16, 1999, now Pat. No. 6,475,521, which is a continuation-in-part of application No. 09/044,446, filed on Mar. 19, 1998, now abandoned.

(51) Int. Cl.
*A61K 9/20* (2006.01)
*A61K 9/22* (2006.01)
*A61K 9/26* (2006.01)
*A61K 31/155* (2006.01)

(52) U.S. Cl. .................. 424/469; 424/468; 424/470; 424/485; 424/486; 424/488; 514/772.3; 514/779; 514/781; 514/951

(58) Field of Classification Search .................. None
See application file for complete search history.

(56) References Cited

To view the complete listing of prior art documents cited during the proceeding for Reexamination Control Number 90/011,872, please refer to the USPTO's public Patent Application Information Retrieval (PAIR) system under the Display References tab.

*Primary Examiner* — Gary Kunz

(57) ABSTRACT

A biphasic controlled release delivery system for pharmaceuticals which have high water solubility, such as the antidiabetic metformin HCl salt, is provided which provides a dosage form that has prolonged gastric residence so that a dosing regimen of at least one gram metformin, once daily, may be achieved while providing effective control of plasma glucose. The delivery system includes (1) an inner solid particulate phase formed of substantially uniform granules containing a pharmaceutical having a high water solubility, and one or more hydrophilic polymers, one or more hydrophobic polymers and/or one or more hydrophobic materials such as one or more waxes, fatty alcohols and/or fatty acid esters, and (2) an outer solid continuous phase in which the above granules of inner solid particulate phase are embedded and dispersed throughout, the outer solid continuous phase including one or more hydrophobic polymers, one or more hydrophobic polymers and/or one or more hydrophobic materials such as one or more waxes, fatty alcohols and/or fatty acid esters, which may be compressed into tablets or filled into capsules. Methods for forming the so-described biphasic controlled release delivery system and using such biphasic controlled release delivery system for treating diabetes are also provided.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 16, 17, 20, 37, 38, 41, 52, 53, 57 and 58 are cancelled.

Claims 1, 27, 48 and 55 are determined to be patentable as amended.

Claims 2-7, 9-11, 13-15, 19, 28-36, 40, 49, 50 and 56, dependent on an amended claim, are determined to be patentable.

Claims 8, 12, 18, 21-26, 39, 42-47, 51, 54, 59 and 60 were not reexamined.

1. A method for treating diabetes comprising administering once daily to a mammalian patient in need of treatment a therapeutically effective amount of a pharmaceutical formulation comprising (1) an inner solid particulate phase, and (2) an outer solid continuous phase in which particles of said inner solid particulate phase are dispersed and embedded, the particles of said inner solid particulate phase comprising (a) a pharmaceutical having a high water solubility selected from metformin or a pharmaceutically acceptable salt thereof; and (b) an extended release material *comprising one or more ionic polymers selected from sodium alginate, carbomer, calcium carboxymethylcellulose and sodium carboxymethylcellulose*, and said outer solid continuous phase comprising an extended release material *comprising one or more non-ionic polymers comprising hydroxypropylmethylcellulose 2208 USP and/or hydroxypropylmethylcellulose 2910 USP*, wherein the total extended release material content in both said inner solid particulate phase and said outer continuous phase is within the range from about 25 to about 75% by weight of the pharmaceutical formulation.

27. A method for treating diabetes comprising administering a pharmaceutical formulation comprising (1) an inner solid particulate phase, and (2) an outer solid continuous phase in which particles of said inner solid particulate phase are dispersed and embedded, the particles of said inner solid particulate phase comprising (a) metformin[or a pharmaceutically acceptable salt thereof], *metformin hydrochloride, metformin succinate (2:1) salt or metformin fumarate (2:1) salt*; and (b) an extended release material *comprising ethyl cellulose and/or sodium carboxymethyl cellulose and/or glyceryl monostearate*, and said outer solid continuous phase comprising an extended release material *comprising hydroxypropymethylcellulose 2208 USP (100,000 cps), and/or hydroxypropylmethylcellulose 2910 USP (5 cps) and/or microcrystalline cellulose*, wherein said extended release material present in said inner solid particulate phase is different from the extended release material present in said outer solid continuous phase and wherein the total extended release material content in both said inner solid particulate phase and said outer solid continuous phase is within the range from about 25 to about 75% by weight of the pharmaceutical formulation.

48. A method of lowering insulin resistance which comprises administering once daily to a mammalian patient in need of such treatment a therapeutically effective amount of a pharmaceutical formulation comprising (1) an inner solid particulate phase, and (2) an outer solid continuous phase in which particles of said inner solid particulate phase are dispersed and embedded, the particles of said inner solid particulate phase comprising (a) a pharmaceutical having a high water solubility selected from metformin or a pharmaceutically acceptable salt thereof; and (b) an extended release material *comprising one or more ionic polymers selected from sodium alginate, carbomer, calcium carboxymethylcellulose and sodium carboxymethylcellulose*, and said outer solid continuous phase comprising an extended release material *comprising one or more non-ionic polymers comprising hydroxypropylmethylcellulose 2208 USP and/or hydroxypropylmethylcellulose 2910 USP*, wherein the total extended release material content in both said inner solid particulate phase and said outer continuous phase is within the range from about 25 to about 75% by weight of the pharmaceutical formulation.

55. A method of lowering insulin resistance which comprises administering to a mammalian patient in need of such treatment a therapeutically effective amount of a pharmaceutical formulation comprising (1) an inner solid particulate phase, and (2) an outer solid continuous phase in which particles of said inner solid particulate phase are dispersed and embedded, the particles of the inner solid particulate phase comprising (a) metformin[or a pharmaceutically acceptable salt thereof], *metformin hydrochloride, metformin succinate (2:1) salt or metformin fumarate (2:1) salt*; and (b) an extended release material *comprising ethyl cellulose and/or sodium carboxymethyl cellulose and/or glyceryl monostearate*, and said outer solid continuous phase comprising an extended release material *comprising hydroxypropylmethylcellulose 2208 USP (100,000 cps), and/or hydroxypropylmethylcellulose 2910 USP (5 cps) and/or microcrystalline cellulose*, wherein the extended release material present in said inner solid particulate phase is different from the extended release material present in said outer solid continuous phase and wherein the total extended release material content in both said inner solid particulate phase and said outer solid continuous phase is within the range from about 25 to about 75% by weight of the pharmaceutical formulation.

* * * * *